(12) United States Patent
Lidgren

(10) Patent No.: US 6,586,009 B1
(45) Date of Patent: Jul. 1, 2003

(54) METHOD FOR MANUFACTURING A POWDER COMPONENT FOR CEMENT FOR MEDICAL USE, USE OF SUCH POWDER COMPONENT AND SUCH POWDER COMPONENT

(75) Inventor: Lars Åke Alvar Lidgren, Lund (SE)

(73) Assignee: Bone Support AB, Tollarp (SE)

( * ) Notice: Subject to any disclaimer, the term of this patent is extended or adjusted under 35 U.S.C. 154(b) by 0 days.

(21) Appl. No.: 09/700,955

(22) PCT Filed: May 27, 1999

(86) PCT No.: PCT/SE99/00896

§ 371 (c)(1),
(2), (4) Date: Nov. 21, 2000

(87) PCT Pub. No.: WO99/62570

PCT Pub. Date: Dec. 9, 1999

(51) Int. Cl.[7] ............ A61K 9/14; A61F 13/00; A61F 2/00
(52) U.S. Cl. ............ 424/489; 424/422; 424/423; 424/426
(58) Field of Search ................ 424/489, 422, 424/9.1, 423, 426; 604/49

(56) References Cited

U.S. PATENT DOCUMENTS 5,650,108 A   7/1997   Nies et al.
5,797,873 A   8/1998   Franz et al.
5,837,752 A * 11/1998  Shastri et al. ............ 424/426

FOREIGN PATENT DOCUMENTS

| EP | 0639382   |   | 2/1995  |
| EP | 0 639 382 | * | 2/1995  |
| EP | 0676212   |   | 10/1995 |
| EP | 0 676 212 | * | 10/1995 |
| EP | 0701824   |   | 3/1996  |
| EP | 0705609   |   | 4/1996  |

* cited by examiner

Primary Examiner—Thurman K. Page
Assistant Examiner—Blessing Fubara
(74) Attorney, Agent, or Firm—Tarolli, Sundheim, Covell & Tummino L.L.P.

(57) ABSTRACT

A method for manufacturing the powder: component for a cement for medical use includes a liquid component containing a polymerizable substance and a powder component containing a plastic substance and an X-ray contrast medium. The liquid component and the powder component are mixed for providing a setting mass which is set to form the cement. In order to prevent the formed cement from releasing particles wearing on articulating or bearing surfaces adjacent ;the point of cementation, a water soluble, non-ionic X-ray contrast medium is mixed with the plastic substance, and for minimizing the risk of damaging the powder component during the sterilization, sterilizing by radiation of the powder component containing the X-ray contrast medium is carried through a negative pressure or in an inert gas atmosphere.

86 Claims, No Drawings

METHOD FOR MANUFACTURING A POWDER COMPONENT FOR CEMENT FOR MEDICAL USE, USE OF SUCH POWDER COMPONENT AND SUCH POWDER COMPONENT

Method for manufacturing a powder component for cement for medical use, use of such powder component and such powder component.

Aseptic loosening is the main long term complication after a total joint replacement. The osteolysis seen in loosening is caused by, in combination, an increased fluid pressure and an increased inflammatoric response to particles, preferably particles of high density polyethylene (HDPE). Another contributing main factor to loosening is related to the prosthetic stability within bone cement or between the cement and bone tissue.

Contrast agents such as barium sulphate ($BaSO_4$) and zirconium dioxide ($ZrO_2$) have been added to cement for medical use to achieve radiographic visibility, i.e. visibility to radiophotography, in order to check the operation result.

In order to improve the interface of cement for medical use, various substances such as e.g. hydroxyapatite and growth factors have been added to the cement. Hydroxyapatite has, inter alia, been used in compositions intended for reduction of the wear caused by fragmentation of the cement, whereby particles of the cement enter the joint cavity, i.e. the implant articulation.

There is today clear evidence that agents impermeable to X-ray emission, i.e., radio opaque agents, which are harder than the metallic counterpart, may cause damages to the articulating surfaces, whereby the wear of the polyethylene increases markedly. In the vast majority of total joint replacement, one of the articulating or bearing surfaces consists namely of a hard, very smooth metallic or ceramic surface, while the other bearing surface is manufactured from high-molecular weight polyethylene. This polyethylene is used as a concave bearing surface. It has been shown that if the radiographic or X-ray contrast media are removed from the bone cement, wear will be reduced. Thus, it is of utmost importance either to abandon said X-ray contrast media, which is disliked by most surgeons, or to find an X-ray contrast medium which will not affect the strength to a greater extent than in existing cements for medical use, but will be less abrasive when fragmented (released) from the cement.

This is possible by using new types of X-ray contrast media, so called non-ionic contrast media. Radiographic or X-ray contrast media of different types with high osmolality and low osmolality are known today. These contrast media have a high affinity for absorbing water and are in fact water soluble. Preliminary experiments regarding the possibility of mixing these X-ray contrast media into bone cement have been carried through in a laboratory and shows that this is possible and that good radiographic visibility, or visibility to radiophotography, is achieved. Studies are also carried through with bone cell cultures in order to study local toxicity. Existing studies show that non-ionic X-ray contrast media, without being added to bone cement, have very low toxicity especially when contrast media having low osmolality are used.

The sterilization procedure is of utmost importance for the production of a new cement for medical use. With the non-ionic, water soluble, radiography or X-ray contrast medium, gas sterilization will induce formation of lumps in the bone cement and sterilization by radiation will be necessary. There is, however, a clear influence by the sterilization upon a range of cement properties. The tensile strength decreases in proportion to the dosage of gamma and beta radiation for the sterilization. The fatigue resistance will also be significantly reduced. Rheology measurements show a large decrease in viscosity and a delay of the setting time after radiation. This effect on acrylic cement by oxidative degradation has been shown to occur also in other polymers, or plastic substances, such as HDPE. If radiation is carried through in air, this will cause extensive oxidation and property deterioration in HDPE. This effect increases with time due to ageing of the material. It has been shown that if radiation is carried through at a negative pressure and/or by means of a protective inert gas, the dominant effect of the radiation will be cross-linking, not degradation. The effect is further improved if the plastic product after sterilization by radiation is subjected to a heat treatment in an environment free of oxygen. Sterilization at a negative pressure and at low temperature also provide improved properties to the polymer.

The object of the present invention is consequently to provide a method for manufacturing the powder component for a cement for medical use in order to prevent the cement obtained from releasing particles which contribute to the wear of articulating or bearing surfaces adjacent the point of cementation as well as minimize the risk of damaging the powder component during sterilisation thereof.

This is arrived at according to the invention by the combination that a water soluble non-ionic X-ray contrast medium is mixed with the plastic substance, whereby particles of the X-ray contrast medium released from the cement after the cementation are dissolved and do not thereby contribute to the wear of articulating or bearing surfaces adjacent the point of cementation, and that sterilisation by radiation of the powder component containing said X-ray contrast medium is carried through at a negative pressure and/or in an inert gas atmosphere in order to minimize the risk of damaging the powder component during the sterilization thereof. The invention also include eventual heat treatment of the powder mixture in the oxygen-free atmosphere after the radiation treatment.

The object of the present invention Is also to render it possible to use the powder component manufactured by said method in a cement which is used as bone cement.

A further object of the invention is to provide a powder component which is manufactured in accordance with the abovementioned method.

Below, a method of manufacturing the powder component for a cement for medical use is described. The cement includes a liquid component containing a polymerisable substance and a powder component containing a plastic substance and an X-ray contrast medium. The liquid and powder components are adapted to be mixed and thereby provide a setting mass which is set to form the cement. A water soluble, non-ionic X-ray contrast medium is mixed with the plastic substance, whereby particles of the X-ray contrast medium released from the cement after cementation are dissolved and do not thereby contribute to the wear of articulating or bearing surfaces adjacent the point of cementation.

Sterilisation by radiation of the powder component containing said X-ray contrast medium is carried through at a negative pressure and/or in an inert gas atmosphere for minimizing the risk of damaging the powder component during the sterilisation.

The water soluble non-ionic X-ray contrast medium which is mixed into the powder component is chosen preferably from the group consisting of iohexol, ioversol, iopamidol, iotrolane, and iodixanol and has preferably low osmolality. Other X-ray contrast media which can be used are metrizamide, iodecimol, ioglucol, ioglucamide, ioglunide, iogulamide, iomeprol, iopentol, iopromide, iosarcol, iosimide, iotasul, ioxilane, iofratol and iodecol. Mixtures of the media can also be used.

EXAMPLE 1

A non-ionic crystalline contrast medium, e.g., iohexol is ground to a powder with a particle diameter of about 4 μm. The powder is then mixed with the plastic substance (polymer) in the powder component to an acrylic cement for medical use, e.g., bone cement, consisting of acrylic polymer particles, preferably polymethylmethacrylate and/or copolymers containing polymethylmethacrylate, with a particle size around 80–100 μm land a very small amount (about 0.5 percent by weight) of a so-called initiator substance, e.g., benzyl peroxide. The X-ray contrast medium comprises preferably about 17–23 percent by weight of the finished powder component (2–3 parts of contrast medium are mixed with 10 parts of the polymer). Other additives can also be added to the powder component. The powder component is then packed up in bag-type portion packs or solid plastic containers, which in both cases are sealed with an air-permeable material, e.g., paper or plastic. The portion packs are placed one by one or in pairs in a further air-permeable bag or container which shall serve as a sterile barrier after sterilization. Prior to sterilization, these packs are placed in an air-proof container, the air is removed such that a negative pressure is generated, corresponding to an air pressure of 5%, preferably about 2.5%, of the atmospheric pressure. Furthermore, or as an alternative thereto, the container may be filled with an inert gas, e.g., argon, and sealed. The content of oxygen in the air-proof container should then be less than 1%, preferably less than 0.5%, of the atmospheric pressure, i.e., the amount of oxygen in the inert gas atmosphere corresponds to a partial pressure of 10 mbar at the most, preferably less than 5 mbar. Sterilization of the powder component is now carried through by radiation, preferably beta or gamma radiation, with a dose of between 0.5 and 7 Mrad, preferably about 2.5 Mrad. After the sterilization by radiation and at the negative pressure/inert gas atmosphere, the powder component may preferably be heated to a temperature of 50–120° C. for 1 min.–24 hours. After the sterilization by radiation, the powder bags should preferably, but not necessarily, be kept in the oxygen-free atmosphere until the cement shall be used.

EXAMPLE 2

As example 1, but where the amount of contrast medium in the powder component is within a range determined by a weight ratio between the contrast medium and polymer of 0,08:1 to 0,6:1 or such that the powder component contains between about 5 and about 40 percent by weight of X-ray contrast medium.

EXAMPLE 3

As examples 1–2, but the particle diameter of the non-ionic contrast medium is within a range of 1–50 μm and of the acrylic polymer particles within a range of 20–200 μm, with the limitation however, that the diameter of the polymer particles is at least four times the diameter of the contrast medium particles.,

EXAMPLE 4

As examples 1–3, where a powder of an antibiotic substance is added to the powder component before the sterilisation.

EXAMPLE 5

As examples 1–4 with addition of a colouring substance, e.g. chlorophyll, to the powder component.

EXAMPLE 6

As examples 1–5, but where the powder component is heated to about 80° C. for one hour after the sterilisation by radiation, still packed in an oxygen-free environment.

EXAMPLE 7

As examples 1–5 except that the powder component is packed directly in a cement mixing container, sealed by means of an air-permeable diaphragm. The cement mixing container filled with powder is packed in an air-permeable pack serving as a sterile barrier. This pack is then placed in an air-proof container, from which the oxygen in the air is evacuated, and sterilisation as in example 1 is carried through.

The powder component manufactured according to the above methods may suitably be used in a bone cement for fixing prostheses or parts of prostheses, but may also be used in cements for other medical purposes.

The powder components produced in accordance with the above examples thus contains a non-ionic X-ray contrast medium and it is sterilised at a negative pressure and/or in an inert gas atmosphere.

In the above methods, the inert gas atmosphere may, except for argon, consist of helium, neon or nitrogen or mixtures thereof.

What is claimed is:

1. Method for manufacturing a powder component for a cement for medical use,
   said cement including a liquid component containing a polymerizable substance and a powder component containing a plastic substance selected from the group consisting of acrylic polymer particles, polymethylmethacrylate and copolymers containing polymethylmethacrylate, and an X-ray contrast medium, and
   wherein the liquid component and the powder component are adapted to be mixed for providing a setting mass which is set to form the cement, said method comprising the steps of:
   mixing a water soluble, non-ionic X-ray contrast medium with the plastic substance selected from the group consisting of acrylic polymer particles, polymethylmethacrylate and copolymers containing polymethylmethacrylate, whereby particles of said X-ray contrast medium released from the cement after cementation are dissolved and do not thereby contribute to the wear of articulating or bearing surfaces adjacent the point of cementation, and
   sterilizing by radiating the powder component containing said X-ray contrast medium at a negative pressure for maintaining the strength of the powder component after the sterilization.

2. The method according to claim 1, including the step of selecting the water soluble, non-ionic X-ray contrast medium from the group consisting of iohexol, ioversol, iopamidol, iotrolane, iodixanol, metrizamide, iodecimol, ioglucol, ioglucamide, ioglunide, iogulamide, iomeprol, iopentol, iopromide, iosarcol, iosimide, iotasul, ioxilane, iofratol and iodecol.

3. The method according to claim 1, wherein the water soluble, non-ionic X-ray contrast medium has a low osmolality.

4. The method according to claim 1, including the step of bringing the powder component to contain a maximum of 40% by weight of water soluble, non-ionic X-ray contrast medium.

5. The method according to claim 4, including the step of bringing the powder component to contain between 5 and 40% by weight of water soluble, non-ionic X-ray contrast medium.

6. The method according to claim 5, including the step of bringing the powder component to contain between 17 and 23% by weight of water soluble, non-ionic X-ray contrast medium.

7. The method according to claim 1, including the step of bringing the water soluble, non-ionic x-ray contrast medium to have a particle diameter of a maximum of 25% of the particle diameter of the plastic substance selected from the group consisting of acrylic polymer particles, polymethylmethacrylate and copolymers containing polymethylmethacrylate.

8. The method according to claim 7, including the step of bringing the water soluble, non-ionic X-ray contrast medium to have a particle diameter of between 1 and 50 $\mu$m, while the particle diameter of the plastic substance[]selected from the group consisting of acrylic polymer particles, polymethylmethacrylate and copolymers containing polymethylmethacrylate is between 20 and 200 $\mu$m.

9. The method according to claim 8, including the step of bringing the water soluble, non-ionic X-ray contrast medium to have a particle diameter of about 5 $\mu$m, while the particle diameter of the plastic substance selected from the group consisting of acrylic polymer particles, polymethylmethacrylate and copolymers containing polymethylmethacrylate is between 80 and 100 $\mu$m.

10. The method according to claim 1, including the step of performing the sterilization by radiation by means of beta or gamma radiation and with a radiation dose of between 0.5 and 7 Mrad 11. The method according to claim 11, including the step of performing the sterilization by radiating at the negative pressure which is below minus 0.95 bar.

12. The method according to claim 11, including the step of performing the sterilization by radiating at the negative pressure which is below minus 0.975 bar.

13. The method according to claim 1, including the step of performing the sterilization by radiating at the negative pressure and at about 77° K.

14. The method according to claim 11, including the step of performing the sterilization by radiating in an inert gas atmosphere, said inert gas atmosphere consisting of argon, helium, neon or nitrogen.

15. The method according to claim 1, including the step of performing the sterilization by radiating in an inert gas atmosphere in which the amount of oxygen corresponds to a partial pressure of 10 mbar at the most.

16. The method according to claim 15, including the step of performing the sterilization by radiating in an inert gas atmosphere in which the amount of oxygen corresponds to a partial pressure of less than 5 mbar.

17. The method according to claim 1, including the step of heating the powder component to 50–120° C. for 1 minute–24 hours after sterilization by radiating at the negative pressure or in an inert gas atmosphere.

18. The method according to claim 1, including the step of adding a substance initiating polymerization to the powder component before the sterilization by radiating.

19. The method according to claim 18, wherein said substance initiating polymerization is benzoyl peroxide.

20. The method according to claim 1, including the step of adding an antibiotic substance to the powder component before the sterilization by radiating.

21. The method according to claim 1, including the step of adding a coburing substance to the powder component before the sterilization by radiating.

22. The method according to claim 21, wherein said coburing substance is chlorophyll.

23. The method according to claim 1, including the step of placing the powder component in an air-permeable container, placing in turn the air-permeable container in an air-proof container, evacuating air from the air-proof container, and sterilizing by radiating the powder component in the air-permeable container.

24. The method according to claim 23, including the step of putting the powder component in a bone cement mixing container.

25. Method for manufacturing a powder component for a cement for medical use, said cement including a liquid component containing a polymerizable substance and a powder component containing a plastic substance selected from the group consisting of acrylic polymer particles, polymethylmethacrylate and copolymers containing polymethylmethacrylate, and an X-ray contrast medium, and wherein the liquid component and the powder component are adapted to be mixed for providing a setting mass which is set to form the cement, said method comprising the steps of:

mixing a water soluble, non-ionic X-ray contrast medium with the plastic substance selected from the group consisting of acrylic polymer particles, polymethylmethacrylate and copolymers containing polymethylmethacrylate, whereby particles of said X-ray contrast medium released from the cement after cementation are dissolved and do not thereby contribute to the wear of articulating or bearing surfaces adjacent the point of cementation, sterilizing by radiating the powder component containing said X-ray contrast medium in an inert gas atmosphere for maintaining the strength of the powder component after the sterilization.

26. The method according to claim 25, including the step of selecting the water soluble, non-ionic X-ray contrast medium from the group consisting of iohexol, ioversol, iopamidol, iotrolane, iodixanol, metrizamide, iodecimol, ioglucol, ioglucamide, ioglunide, iogulamide, iomeprol, iopentol, iopromide, iosarcol, iosimide, iotasul, ioxilane, iofratol and iodecol.

27. The method according to claim 25, wherein the water soluble, non-ionic X-ray contrast medium has a low osmolality.

28. The method according to claim 25, including the step of bringing the powder component to contain a maximum of 40% by weight of water soluble, non-ionic X-ray contrast medium.

29. The method according to claim 28, including the step of bringing the powder component to contain between 5 and 40% by weight of water soluble, non-ionic X-ray contrast medium.

30. The method according to claim 29, including the step of bringing the powder component to contain between 17 and 23% by weight of water soluble, non-ionic X-ray contrast medium.

31. The method according to claim 25, including the step of bringing the water soluble, non-ionic X-ray contrast medium to have a particle diameter of a maximum of 25% of the particle diameter of the plastic substance selected from the group consisting of acrylic polymer particles, polymethylmethacrylate and copolymers containing polymethylmethacrylate.

32. The method according to claim 31, including the step of bringing the water soluble, non-ionic X-ray contrast medium to have a particle diameter of between 1 and 50 µm, while the particle diameter of the plastic substance selected from the group consisting of acrylic polymer particles, polymethylmethacrylate and copolymers containing polymethylmethacrylate is between 20 and 200 µm.

33. The method according to claim 32, including the step of bringing the water soluble, non-ionic X-ray contrast medium to have a particle diameter of about 5 µm, while the particle diameter of the plastic substance selected from the group consisting of acrylic polymer particles, polymethylmethacrylate and copolymers containing polymethylmethacrylate is between 80 and 100 µm.

34. The method according to claim 25, including the step of performing the sterilization by radiation by means of beta or gamma radiation and with a radiation dose of between 0.5 and 7 Mrad.

35. The method according to claim 25, including the step of performing the sterilization by radiating at the negative pressure which is below minus 0.95 bar.

36. The method according to claim 35, including the step of performing the sterilization by radiating at the negative pressure which is below minus 0.975 bar.

37. The method according to claim 25, including the step of performing the sterilization by radiating at the negative pressure and at about 77° K.

38. The method according to claim 25, including the step of performing the sterilization by radiating in an inert gas atmosphere, said inert gas atmosphere consisting of argon, helium, neon or nitrogen.

39. The method according to claim 25, including the step of performing the sterilization by radiating in an inert gas atmosphere in which the amount of oxygen corresponds to a partial pressure of 10 mbar at the most.

40. The method according to claim 39, including the step of performing the sterilization by radiating in an inert gas atmosphere in which the amount of oxygen corresponds to a partial pressure of less than 5 mbar.

41. The method according to claim 25, including the step of heating the powder component to 50–120° C. for 1 minute–24 hours after sterilization by radiating and at the negative pressure or in an inert gas atmosphere.

42. The method according to claim 25, including the step of adding a substance initiating polymerization to the powder component before the sterilization by radiating.

43. The method according to claim 42, wherein said substance initiating polymerization is benzoyl peroxide.

44. The method according to claim 25, including the step of adding an antibiotic substance to the powder component before the sterilization by radiating.

45. The method according to claim 25, including the step of adding a coburing substance to the powder component before sterilization by radiating.

46. The method according to claim 45, wherein the coburing substance is chlorophyll.

47. The method according to claim 25, including the step of placing the powder component in an air-permeable container, placing in turn the air-permeable container in an air-proof container, evacuating air from the air-proof container, and sterilizing by radiating the powder component in the air-permeable container.

48. The method according to claim 47, including the step of putting the powder component in a bone cement mixing container.

49. Method for manufacturing a powder component for a cement for medical use, said cement including a liquid component containing a polymerizable substance and a powder component containing a plastic substance selected from the group consisting of acrylic polymer particles, polymethylmethacrylate and copolymers containing polymethylmethacrylate, and an X-ray contrast medium, and wherein the liquid component and the powder component are adapted to be mixed for providing a setting mass which is set to form the cement, said method comprising the steps of:

mixing a water soluble, non-ionic X-ray contrast medium with the plastic substance selected from the group consisting of acrylic polymer particles, polymethylmethacrylate and copolymers containing polymethylmethacrylate, whereby particles of said X-ray contrast medium released from the cement after cementation are dissolved and do not thereby contribute to the wear of articulating or bearing surfaces adjacent the point of cementation, sterilizing by radiating the powder component containing said X-ray contrast medium at a negative pressure and in an inert gas atmosphere for maintaining the strength of the powder component after the sterilization.

50. The method according to claim 49, including the step of selecting the water soluble, non-ionic X-ray contrast medium from the group consisting of iohexol, ioversol, iopamidol, iotrolane, iodixanol, metrizamide, iodecimol, ioglucol, ioglucamide, ioglunide, iogulamide, iomeprol, iopentol, iopromide, iosarcol, iosimide, iotasul, ioxilane, iofratol and iodecol.

51. The method according to claim 49, wherein the water soluble, non-ionic X-ray contrast medium has a low osmolality.

52. The method according to claim 49, including the step of bringing the powder component to contain a maximum of 40% by weight of water soluble, non-ionic X-ray contrast medium.

53. The method according to claim 52, including the step of bringing the powder component to contain between 5 and 40% by weight of water soluble, non-ionic X-ray contrast medium.

54. The method according to claim 53, including the step of bringing the powder component to contain between 17 and 23% by weight of water soluble, non-ionic X-ray contrast medium.

55. The method according to claim 49, including the step of bringing the water soluble, non-ionic X-ray contrast medium to have a particle diameter of a maximum of 25% of the particle diameter of the plastic substance selected from the group consisting of acrylic polymer particles, polymethylmethacrylate and copolymers containing polymethylmethacrylate.

56. The method according to claim 55, including the step of bringing the water soluble, non-ionic X-ray contrast medium to have a particle diameter of between 1 and 50 µm, while the particle diameter of the plastic substance selected from the group consisting of acrylic polymer particles, polymethylmethacrylate and copolymers containing polymethylmethacrylate is between 20 and 200 μm.

57. The method according to claim 56, including the step of bringing the water soluble, non-ionic X-ray contrast medium to have a particle diameter of about 5 μm, while the particle diameter of the plastic substance selected from the group consisting of acrylic polymer particles, polymethylmethacrylate and copolymers containing polymethylmethacrylate is between 80 and 100 μm.

58. The method according to claim 49, including the step of performing the sterilization by radiation by means of beta or gamma radiation and with a radiation dose of between 0.5 and 7 Mrad.

59. The method according to claim 49, including the step of performing the sterilization by radiating at the negative pressure which is below minus 0.95 bar.

60. The method according to claim 59, including the step of performing the sterilization by radiating at the negative pressure which is below minus 0.975 bar.

61. The method according to claim 49, including the step of performing the sterilization by radiating at the negative pressure and at about 77° K.

62. The method according to claim 49, including the step of performing the sterilization by radiating in an inert gas atmosphere, said inert gas atmosphere consisting of argon, helium, neon or nitrogen.

63. The method according to claim 49, including the step of performing the sterilization by radiating in an inert gas atmosphere in which the amount of oxygen corresponds to a partial pressure of 10 mbar at the most.

64. The method according to claim 63, including the step of performing the sterilization by radiating in an inert gas atmosphere in which the amount of oxygen corresponds to a of partial pressure of less than 5 mbar.

65. The method according to claim 49, including the step of heating the powder component to 50–120° C. for 1 minute–24 hours after sterilization by radiating and at the negative pressure or an inert atmosphere.

66. The method according to claim 49, including the step of adding a substance initiating polymerization to the powder component before the sterilization by radiating.

67. The method according to claim 66, wherein said substance initiating polymerization is benzoyl peroxide.

68. The method according to claim 49, including the step of adding an antibiotic substance to the powder component before the sterilization by radiating.

69. The method according to claim 49, including the step of adding a coburing substance to the powder component before the sterilization by radiating.

70. The method according to claim 69, wherein the coburing substance is chlorophyll.

71. The method according to claim 49, including the step of placing the powder component in an air-permeable container, placing in turn the air-permeable container in an air-proof container, evacuating air from the air-proof container, and sterilizing by radiating the powder component in the air-permeable container.

72. The method according to claim 71, including the step of putting the powder component in a bone cement mixing container.

73. A powder component for cement for medical use comprising:

a water soluble, non-ionic X-ray contrast medium, and a plastic substance selected from the group consisting of acrylic polymer particles, polymethylmethacrylate and copolymers containing polymethylmethacrylate, sterilized at one of a negative pressure and in an inert gas atmosphere.

74. The powder component according to claim 73, wherein the water soluble, non-ionic X-ray contrast medium is selected from the group consisting of iohexol, ioversol, iopamidol, iotrolane, iodixanol, metrizamide, iodecimol, ioglucol, ioglucamide, ioglunide, igolumaide, iomeptro, iopentol, iopromide, iosarcol, iosimide, iotasul, ioxilane, iofratol, and iodecol.

75. The powder component according to claim 74, wherein said powder component contains maximum of 40% by weight of water soluble, non-ionic X-ray contrast medium.

76. The powder component according to claim 75, wherein said powder component contains between 5 and 40% by weight of water soluble, non-ionic X-ray contrast medium.

77. The powder component according to claim 76, wherein said powder component contains between 17 and 23% by weight of water soluble, non-ionic X-ray contrast medium.

78. The powder component according to claim 73, wherein said water soluble, non-ionic X-ray contrast medium has a particle diameter of maximum 25% of the particle diameter of a plastic substance selected from the group consisting of acrylic polymer particles, polymethylmethacrylate and copolymers containing polymethylmethacrylate.

79. The powder component according to claim 73, wherein said water soluble, non-ionic X-ray contrast medium has a particle diameter of between 1 and 50 μm, while the particle diameter of the plastic substance selected from the group consisting of acrylic polymer particles, polymethylmethacrylate and copolymers containing polymethylmethacrylate is between 20 and 200 μm.

80. The powder component according to claim 79, wherein said water soluble, non-ionic X-ray contrast medium has a particle diameter of about 5 μm, while the particle diameter of a plastic substance selected from the group consisting of acrylic polymer particles, polymethylmethacrylate and copolymers containing polymethylmethacrylate is between 80 and 100 μm.

81. The powder component according to claim 73, wherein said powder component contains an antibiotic substance.

82. The powder component according to claim 73, wherein said powder component contains a coburing substance.

83. The powder component according to claim 82, wherein said coburing substance is chlorophyll.

84. The powder component according to claim 73, wherein the negative pressure is about 5% of atmospheric pressure.

85. The powder component according to claim 84, wherein the negative pressure corresponds to about 2.5% of atmospheric pressure.

86. The powder component according to claim 73, wherein the inert gas is selected from the group consisting of argon, helium, neon, and nitrogen.

* * * * *